United States Patent [19]

Jager et al.

[11] 3,997,573
[45] Dec. 14, 1976

[54] SAPONIFICATION OF 1-ACETAMINO-ANTHRAQUINONE

[75] Inventors: Horst Jager, Leverkusen; Erich Klauke, Odenthal, both of Germany

[73] Assignee: Bayer Aktiengesellschaft, Leverkusen, Germany

[22] Filed: Mar. 18, 1976

[21] Appl. No.: 668,164

[30] Foreign Application Priority Data

Mar. 26, 1975   Germany .......................... 2513254

[52] U.S. Cl. ............................................ 260/378
[51] Int. Cl.$^2$ .................... C09B 1/16; C07C 97/12; C07C 97/24
[58] Field of Search .................................. 260/378

[56] References Cited
FOREIGN PATENTS OR APPLICATIONS

| 192,201 | 10/1907 | Germany | 260/378 |
| 203,752 | 10/1908 | Germany | 260/378 |
| 199,713 | 6/1908 | Germany | 260/378 |
| 263,946 | 1/1927 | United Kingdom | 260/378 |

OTHER PUBLICATIONS

Ullmann, "Enzyklopadie der Technischen Chemie", 3rd Ed., vol. 3, p. 685, vol. 7, p. 593, 1973.

*Primary Examiner*—Paul F. Shaver
*Attorney, Agent, or Firm*—Burgess, Dinklage & Sprung

[57]   ABSTRACT

In the saponification of 1-acetamino-anthraquinone to produce the corresponding 1-amino-anthraquinone, the improvement which comprises effecting the saponification with aqueous alkali such as a hydroxide, oxide or carbonate of an alkali metal or an oxide or hydroxide of an alkaline earth metal. The saponification is effected in water, which may contain an organic solvent such as alcohol.

12 Claims, No Drawings

SAPONIFICATION OF 1-ACETAMINO-ANTHRAQUINONE

The present invention relates to a process for the preparation of 1-amino-anthraquinone by the route of alkaline saponification of 1-acetamino-anthraquinone.

From Ber. 38,2,866 (1905) it is knowwn to prepare 1-amino-anthraquinone by boiling 1-acetamino-anthraquinone with hydrochloric acid. Collection Czechoslov. Chem. Commun. 27, 46 (1962) describes the saponification of acetyl- and benzoylamino-anthraquinone to 1-amino-anthraquinone using concentrated hydrochloric acid at elevated temperature.

It has now been found that 1-amino-anthraquinone is obtained in a technically advantageous manner by saponification of 1-acetamino-anthraquinone if the saponification is carried out in an aqueous/alkaline medium, optionally with addition of a solvent.

This was surprising insofar as it was known from Ullman, Enzykylopadie der technischen Chemie (Encyclopaedia of Industrial Chemistry), 3rd Edition, Volume 3, page 685 that the treatment of 1-acetamino-anthraquinone with alkaline agents leads to 1,9-anthrapyridone. This is supported by British Patent No. 263,946 which also discloses that reaction of acetyl amino anthraquinone with aqueous caustic at the boil produces the corresponding anthrapyridone. To the same effect is German Patent No. 192,201 which discloses that cooking of acetylated secondary aminoanthraquinones with dilute caustic at the boil produces the corresponding anthrapyridones. German Patent No. 203,752 discloses that simple acetylaminoanthraquinone in nitrobenzene well below the boil when cooked with alkali produces the corresponding anthrapyridone. German Patent No. 199,713 teaches that the formation of anthrapyridones according to German Patent No. 192,201 extends to sulfonated acetaminoanthraquinones as well. It would appear these effects are specific to acetaminoanthraquinones since Ullmann, 4th Edition, Vol. 7, page 593 states that 4,8-bis-benzoylamino-1-hydroxyanthraquinone when contacted with alkali under unspecified temperature and pressure loses the 8-benzoyl moiety. Clearly though one could not have expected the instant reaction conditions to produce the indicated results.

1-Acetamino-anthraquinone is in itselve known. Its preparation is described, for example, in Else vier's Encyclopedia Series III, Volume 13, Tricyclic compounds, page 442.

The process according to the invention can be used particularly advantageously on 1-acetamino-anthraquinone which have been obtained by the route of saponification of the lactam of 2-amino-2′-carboxydiphenylmethane, acetylation of the saponification product, cyclization of the 2-acetamino-2′-carboxydiphenylmethane thus obtained to the 4-acetaminoanthrone and oxidation thereof to the 1-acetamino-anthraquinone. The lactam and its saponification are known and described, for example, in Liebig's Annalen der Chemie 594, 89 (1955). The subsequent acetylation is then carried out in a manner familiar to those skilled in the art. For cyclization the acetylation product is, for example, introduced into sulfuric acid (monohydrate) at 30° – 40° C and the reaction mixture is left at this temperature for 1 to 3 hours. The resulting reaction mixture can then be discharged onto ice and 4-acetaminoanthrone obtained as a solid residue. The 4-acetaminoanthrone can then be oxidized in aqueous suspension with hydrogen peroxide in the presence of sodium silicate, to give the 1-acetamino-anthraquinone, which can then be subjected to the process according to the invention.

Compounds which can be used to adjust the alkalinity within the scope of the process according to the invention are all compounds having an alkaline reaction which are in themselves known. Examples which may be mentioned are the hydroxides, oxides and carbonates of the alkali metals and the oxides and hydroxides of the alkaline earth metals. Examples of individual compounds which may be mentioned are: sodium hydroxide, potassium hydroxide, magnesium hydroxide, calcium hydroxide, potassium carbonate and sodium carbonate.

These compounds having an alkaline reaction are added in at least the stoichiometrically required amount and generally in amounts of about 1.1 to 5 times the stoichiometric amount of 1-acet-amino-anthraquinone. The addition of about 1.3 to 2 times the stoichiometric amount is preferred.

The saponification can be carried out in the aqueous phase alone or in a mixture of water and an organic solvent, it being possible, for example, to employ the 3- to 10-fold amount of water relative to 1-acetamino-anthraquinone Examples of organic solvents which may be mentioned are: aliphatic alcohols with up to 6 carbon atoms, for example methanol, ethanol and isopropanol. Other organic solvents which can be used are ethers, such as diisopropyl ether, tetrahydrofurane and dioxane, and aromatic hydrocarbons which are optionally substituted by halogen, alkyl or alkoxy, such as benzene, toluene, xylene, chlorobenzene and anisole.

The compounds having an alkaline reaction can be added to the reaction mixture in the form of their aqueous solutions. When the reaction is carried out in the aqueous phase they can also be added in the solid form. For example, the reaction can be carried out with calcium hydroxide in suspension.

When carrying out the process according to the invention the procedure is generally such that the 1-acetamino-anthraquinone, in water or a mixture of water and solvent, is initially introduced and the compound having an alkaline reaction is then added and the reaction mixture thus obtained is warmed. The reaction temperature can vary within wide limits, the mixture generally being warmed to temperatures of about 60° to 200° C. When the reaction is carried out in the presence of an alcohol, temperatures between about 70° and 100° C, especially between about 80° and 100° C, will generally be selected, while when the reaction is carried out in the aqueous phase alone, temperatures above about 100° C, especially of about 120° to 180° C, have proved advantageous. The process according to the invention can be carried out both under normal pressure and under elevated pressure.

If the reaction is carried out in the aqueous phase, the 1-amino-anthraquinone can be separated by filtering off the alkaline saponification liquor. After washing off the adhering mother liquor with water, 97 to 98% pure 1-aminoanthraquinone is obtained. If the saponification is carried out in methanol or ethanol, the isolation and working up can be carried out in the same way. The degree of purity of the 1-amino-anthraquinone is then between 97 and 99%. In this case it is also possible, by concentrating the mother liquor, to obtain a small amount of a 1-amino-anthraquinone which is not quite pure.

The process according to the invention enables 1-amino-anthraquinone to be prepared in high purity, which is the decisive pre-requisite for further processing of the intermediate product 1-amino-anthraquinone to the particular dyestuffs (see, for example, FIAT Final Report No. 1,313, page 23).

The invention will be further described in the following illustrative examples wherein all parts are by weight unless otherwise expressed.

EXAMPLE 1

363 g (1.37 moles) of 1-acetamino-anthraquinone are stirred into 3.5 kg of ethanol, 150 ml of concentrated sodium hydroxide solution ($d = 1.48$) are added and the mixture is then heated to the reflux temperature (80° C) for three hours. After cooling to 15° C, the red suspension is suction filtered. The residue is washed on the suction filter with hot water until the filtrate has a neutral reaction. After drying, 291 g of 1-amino-anthraquinone are obtained (yield: 95.2%). Degree of purity: 98 to 99%.

EXAMPLE 2

363 g (1.37 moles) of 1-acetamino-anthraquinone are warmed with 3.5 kg of methanol and 150 ml of concentrated sodium hydroxide solution ($d = 1.48$) in a stainless steel autoclave for 3 hours at 85° C. After cooling to room temperature, the red suspension is suction filtered. The residue on the suction filter is washed with hot water until the filtrate has a neutral reaction. After drying, 290 g of 1-amino-anthraquinone are obtained (yield: 95%). Degree of purity: 98 to 99%.

EXAMPLE 3

363 g (1.37 moles) of 1-acetamino-anthraquinone are warmed with 3.5 l of water and 130 ml of concentrated sodium hydroxide solution ($d = 1.48$) in a stainless steel autoclave for 5 hours at 150° C. After cooling to room temperature, the red suspension is filtered. The residue is washed with hot water until neutral. After drying, 300 g of 1-amino-anthraquinone are obtained (yield: 98%). Degree of purity: 97 to 98%.

It will be appreciated that the instant specification and examples are set forth by way of illustration and not limitation, and that various modifications and changes may be made without departing from the spirit and scope of the present invention.

What is claimed is:

1. In the saponification of 1-acetamino-anthraquinone to produce 1-amino-anthraquinone, the improvement which comprises effecting the saponification with aqueous alkali.

2. A process according to claim 1, in which the saponification is carried out at a temperature of up to about 200° C.

3. A process according to claim 1, in which the saponification is carried out with the addition of a solvent.

4. A process according to claim 3, in which the additional solvent is an alcohol.

5. A process according to claim 4, in which the alcohol is methanol, ethanol or isopropanol.

6. A process according to claim 5, in which the saponification is carried out at a temperature of about 70° to 100° C.

7. A process according to claim 1, in which the saponification is effected, in the absence of any additional organic solvent, at a temperature of about 120° to 180° C.

8. A process according to claim 1, in which the alkali is selected from the group consisting of a hydroxide, oxide or carbonate of an alkali metal and an oxide or hydroxide of an alkaline earth metal.

9. A process according to claim 1, in which the alkali is sodium hydroxide.

10. A process according to claim 1, in which the alkali is present in about 1.1 to 5 times the stoichiometric amount of the 1-acetamino-anthraquinone.

11. A process according to claim 10, in which the alkali is sodium hydroxide and the saponification is carried out in the absence of an additional organic solvent and at a temperature of above 100° C.

12. A process according to claim 11, in which the saponification is carried out at a temperature of about 120° – 180° C.

* * * * *